US011583684B2

(12) United States Patent
Carcieri et al.

(10) Patent No.: US 11,583,684 B2
(45) Date of Patent: Feb. 21, 2023

(54) SYSTEMS AND METHODS FOR VISUALIZING AND PROGRAMMING ELECTRICAL STIMULATION

(71) Applicant: Boston Scientific Neuromodulation Corporation, Valencia, CA (US)

(72) Inventors: Stephen Carcieri, Los Angeles, CA (US); Vikrant Venkateshwar Gunna Srinivasan, Los Angeles, CA (US); Chirag Shah, Valencia, CA (US); Peter J. Yoo, Burbank, CA (US); Michael A. Moffitt, Solon, OH (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 17/683,974

(22) Filed: Mar. 1, 2022

(65) Prior Publication Data

US 2022/0176135 A1 Jun. 9, 2022

Related U.S. Application Data

(63) Continuation of application No. 16/396,285, filed on Apr. 26, 2019, now Pat. No. 11,285,329.

(Continued)

(51) Int. Cl.
*A61N 1/02* (2006.01)
*A61N 1/05* (2006.01)
*A61N 1/372* (2006.01)

(52) U.S. Cl.
CPC ......... *A61N 1/37235* (2013.01); *A61N 1/025* (2013.01); *A61N 1/0529* (2013.01);
(Continued)

(58) Field of Classification Search
CPC .... A61N 2/002; A61N 1/0551; A61N 1/3605; A61N 1/36135; A61N 1/0484;
(Continued)

(56) References Cited

U.S. PATENT DOCUMENTS 3,999,555 A 12/1976 Person
4,144,889 A 3/1979 Tyers et al.
(Continued)

FOREIGN PATENT DOCUMENTS

EP 1048320 11/2000
EP 1166819 1/2002
(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005),319-30.
(Continued)

*Primary Examiner* — Carl H Layno
*Assistant Examiner* — Anh-Khoa N Dinh
(74) *Attorney, Agent, or Firm* — Branch Partners PLLC; Bruce E. Black

(57) ABSTRACT

Methods and systems can facilitate visualizing cathodic and anodic stimulation separately via displaying and modifying graphical representations of anodic and cathodic volumes of activation. Alternately, the methods and systems may separately visualize stimulation of different neural elements, such as nerve fibers and neural cells. These methods and systems can further facilitate programming an electrical stimulation system for stimulating patient tissue.

20 Claims, 10 Drawing Sheets

Related U.S. Application Data

(60) Provisional application No. 62/663,895, filed on Apr. 27, 2018.

(52) U.S. Cl.
CPC .......... *A61N 1/0551* (2013.01); *A61N 1/0507* (2013.01); *A61N 1/37217* (2013.01)

(58) Field of Classification Search
CPC .. A61N 5/0622; A61N 1/37235; A61N 1/025; A61N 1/0529; A61N 1/0507; A61N 1/37217; A61N 1/36071; A61N 1/36185; A61N 1/37247; A61N 1/0534; A61N 1/36021; A61N 1/36139; A61N 1/3787; A61N 1/36182; A61N 1/36132; A61N 1/36128; A61N 1/36175; A61N 1/0492
See application file for complete search history.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |

(56) References Cited

U.S. PATENT DOCUMENTS

| | | |
|---|---|---|
| 7,054,692 B1 | 5/2006 | Whitehurst et al. |
| 7,136,518 B2 | 5/2006 | Griffin et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,282 B2 | 3/2008 | Sakanaka et al. |
| 7,346,382 B2 | 3/2008 | McIntyre et al. |
| 7,388,974 B2 | 6/2008 | Yanagita |
| 7,437,193 B2 | 10/2008 | Parramon et al. |
| 7,450,997 B1 | 11/2008 | Pianca et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,209,027 B2 | 6/2012 | Butson et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,429,174 B2 | 4/2013 | Ramani et al. |
| 8,452,415 B2 | 5/2013 | Goetz et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,589,316 B2 | 11/2013 | Lujan et al. |
| 8,594,800 B2 | 11/2013 | Butson et al. |
| 8,606,360 B2 | 12/2013 | Butson et al. |
| 8,620,452 B2 | 12/2013 | King et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,958,615 B2 | 2/2015 | Blum et al. |
| 9,020,789 B2 | 4/2015 | Butson et al. |
| 9,050,470 B2 | 6/2015 | Carlton et al. |
| 9,072,905 B2 | 7/2015 | Kokones et al. |
| 9,248,272 B2 | 2/2016 | Romero |
| 9,623,250 B2 | 4/2017 | Lee et al. |
| 10,112,050 B2 | 10/2018 | Lee et al. |
| 10,398,900 B2 | 9/2019 | Lee et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |

(56) References Cited

U.S. PATENT DOCUMENTS

| | | |
|---|---|---|
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0076535 A1 | 3/2010 | Pianca et al. |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0066407 A1 | 3/2011 | Butson et al. |
| 2011/0078900 A1 | 4/2011 | Pianca et al. |
| 2011/0093045 A1 | 4/2011 | Moffitt |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0238129 A1 | 9/2011 | Moffitt |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |

(56) References Cited

U.S. PATENT DOCUMENTS

| | | |
|---|---|---|
| 2012/0089205 A1 | 4/2012 | Boyden et al. |
| 2012/0101552 A1 | 4/2012 | Lazarewicz et al. |
| 2012/0109257 A1* | 5/2012 | Yoo .................. A61N 1/37247 607/59 |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0239115 A1* | 9/2012 | Lee .................... A61N 1/37247 607/59 |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316615 A1 | 12/2012 | Digiore et al. |
| 2012/0316619 A1 | 12/2012 | Goetz et al. |
| 2012/0330622 A1 | 12/2012 | Butson et al. |
| 2013/0039550 A1 | 2/2013 | Blum et al. |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0289380 A1 | 10/2013 | Molnar et al. |
| 2013/0289660 A1 | 10/2013 | Molnar et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0122379 A1 | 5/2014 | Moffitt et al. |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0005842 A1 | 1/2015 | Lee et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0134031 A1 | 5/2015 | Moffitt et al. |
| 2015/0151113 A1 | 6/2015 | Govea et al. |
| 2016/0001087 A1 | 1/2016 | Moffitt |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0228692 A1 | 8/2016 | Steinke et al. |
| 2016/0256693 A1 | 9/2016 | Parramon |
| 2016/0346557 A1 | 12/2016 | Bokil |
| 2016/0375248 A1 | 12/2016 | Carcieri et al. |
| 2016/0375258 A1* | 12/2016 | Steinke ............. A61N 1/37241 607/59 |
| 2017/0100593 A1 | 4/2017 | Zottola |
| 2017/0100601 A1 | 4/2017 | Xiao et al. |
| 2017/0106197 A1 | 4/2017 | Wechter et al. |
| 2017/0252570 A1 | 9/2017 | Serrano Carmona et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/006304 | 1/2010 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |
| WO | 2016/081099 | 5/2016 |

OTHER PUBLICATIONS

Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.

Butson et al.. "Current Steering to control the volume of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysiol. 21 (1 ). (Jan.-Feb. 2004 ),40-50.

(56) References Cited

OTHER PUBLICATIONS

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
Plaha, P., et al., "Stimulation of the caudal zona incerta is superior to stimulation of the subthalamic nucleus in improving contralateral parkinsonism.", Brain 129{Pt 7) (Jul. 2006), 1732-4 7.
Rattay, F, "Analysis of models for external stimulation of axons", IEEE Trans. Biomed. Eng. vol. 33 (1986),974-977.
Rattay, F., "Analysis of the electrical excitation of CNS neurons", IEEE Transactions on Biomedical Engineering 45(6). (Jun. 1998),766-772.
Rose, T. L., et al., "Electrical stimulation with Pt electrodes. VIII. Electrochemically safe charge injection limits with 0.2 ms pulses [neuronal application]", IEEE Transactions on Biomedical Engineering, 37(11}, (Nov. 1990), 1118-1120.
Rubinstein, J. T., et al., "Signal coding in cochlear implants: exploiting stochastic effects of electrical stimulation", Ann Otol Rhinol Laryngol Suppl . . . 191, (Sep. 2003), 14-9.
Schwan, H.P., et al., "The conductivity of living tissues.", Ann NY Acad Sci., 65(6). (Aug. 1957),1007-13.
Taylor, R. S., et al., "Spinal cord stimulation for chronic back and leg pain and failed back surgery syndrome: a systematic review and analysis of prognostic factors", Spine 30(1 ). (Jan. 1, 2005), 152-60.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments—electrochemical considerations.", J Neurosci Methods, 142(2), (Mar. 30, 2005),251-65.
Vidailhet, M., et al., "Bilateral deep-brain stimulation of the globus pallidus in primary generalized dystonia", N Engl J Med. 352(5) (Feb. 3, 2005),459-67.
Izad, Oliver, "Computationally Efficient Method in Predicating Axonal Excitation," Dissertation for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturelles (1901), 37:547-579.
Dice, Lee R., "Measures of the Amount of Ecologic Association Between Species," Ecology 26(3) (1945): 297-302. doi:10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/BF01908075.
Cover, T.M. et al., "Elements of information theory," (1991) John Wiley & Sons, New York, NY.
Meila, Marina, "Comparing Clusterings by the Variation of Information," Learning Theory and Kernel Machines (2003): 173-187.
Viola, P., et al., "Alignment by maximization of mutual information", International Journal of Com outer Vision 24(2). ( 1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the Volume of Tissue Activated During Deep Brain Stimulation," Journal of Neural Engineering, Mar. 1, 2006, vol. 3, No. 1, pp. 1-8.

Volkmann et al., Indroduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J., et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004),719-28.
Wei, X. F., et al., "Current density distributions, field distributions and impedance analysis of segmented deep brain stimulation electrodes", J Neural Eng . . . 2(4). (Dec. 2005), 139-47.
Zonenshayn, M., et al., "Location of the active contact within the subthalamic nucleus (STN) in the treatment of idiopathic Parkinson's disease ", Surg Neurol., 62(3) (Sep. 2004),216-25.
Da Silva et al (A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37:204-10 (Aug. 2005).
Moss, J., et al., "Electron microscopy of tissue adherent to explanted electrodes in dystonia and Parkinson's disease", Brain, 127{Pt 12). (Dec. 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12:// www.sci.utah.edu/cibc/software/index.html, MCRR Center for Integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, p. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.

(56) References Cited

OTHER PUBLICATIONS

Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M., et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C., et al., "Postoperative Monitoring of the Electrical Properties of Tissue and Electrodes in Deep Brain Stimulation", Neuromodulation, 6(4), (Oct. 2003),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus (Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C., et al., "Modeling extracellular field potentials and the frequency-filtering properties of extracellular space", Biophys J . . . 86(3). (Mar. 2004),1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention—Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp. 603-608.

Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging," Magn. Reson. Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of afterpotentials on the recovery cycle," J Neurophysiol, 87(2) (Feb. 2002), pp. 995-1006.
Mcintyre, Cameron C., et al., "Selective microstimulation of central nervous system neurons," Annals of biomedical engineering, 28(3) (Mar. 2000), pp. 219-233.
Mcintyre, C. C., et al., "Sensitivity analysis of a model of mammalian neural membrane," Biol Cybern., 79(1) (Jul. 1998), pp. 29-37.
Mcintyre, Cameron C., et al., "Uncovering the mechanism(s) of action of deep brain stimulation: activation, inhibition, or both," Clin Neurophysiol, 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.
Alo, K. M., et al., "New trends in neuromodulation for the management of neuropathic pain," Neurosurgery, 50(4), (Apr. 2002), pp. 690-703, discussion pp. 703-704.

(56) References Cited

OTHER PUBLICATIONS

Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Ocl. 2002), pp. 969-983.
Bammer, R, et al., "Diffusion tensor imaging using single-shot SENSE-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16(6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Dasilva, A.F. M., et al., "A Primer Diffusion Tensor Imaging of Anatomical Substructures," Neurosurg. Focus; 15(1) (Jul. 2003), pp. 1-4.
Dawant, B. M., et al., "Compuerized atlas-guided positioning of deep brain stimulators: a feasibility study," Biomedical Image regislialion, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atalas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes in Computer Science; vol. 2489 (2002), pp. 69-76.

Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al.,"Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.

(56) References Cited

OTHER PUBLICATIONS

D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural, 65:612-616, May 2008.
McIntyre, Cameron , et al., "Finite element analysis of the current-density and electric field generated by metal microelectrodes", Ann Biomed Eng . 29(3), (2001 ),227-235.
Foster, K. R., et al., "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med . . . 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr. 1, 2000),45-50.
Hines, M. L., et al., "The NEURON simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9) (Sep. 2004),1050-4.
Hershey, T., et al., "Cortical and subcortical blood flow effects of subthalamic nucleus stimulation in PD.", Neurology 61(6). (Sep. 23, 2003),816-21.
Hemm, S. , et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EEG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3) (Nov. 15, 2005),598-606.
Hashimoto, T. , et al., "Stimulation of the subthalamic nucleus changes the firing pattern of pallidal neurons", J Neurosci. 23(5). (Mar. 1, 2003),1916-23.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
McNaughtan et al., "Electrochemical Issues in Impedance Tomography", 1st World Congress on Industrial Process Tomography, Buxton, Greater Manchester, Apr. 14-17, 1999.
Grill, WM., et al., "Electrical properties of implant encapsulation tissue", Ann Biomed Eng. vol. 22. (1994),23-33.
Grill, W. M., et al., "Deep brain stimulation creates an informational lesion of the stimulated nucleus", Neuroreport. 15I7t (May 19, 2004 ), 1137-40.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-32.
International Search Report and Written Opinion for PCT/US2019/029397 dated Jun. 25, 2019.
Kirsch AD, Hassin-Baer S, Matthies C, Volkmann J, Steigerwald F. "Anodic versus cathodic neurostimulation of the subthalamic nucleus: A randomized-controlled study of acute clinical effects." Parkinsonism and Related Disorders 55 (2018) 61-67.
Official Communication for U.S. Appl. No. 16/396,285 dated Sep. 21, 2020.
Official Communication for U.S. Appl. No. 16/396,285 dated Nov. 18, 2020.
Official Communication for U.S. Appl. No. 16/396,285 dated Apr. 30, 2021.
Official Communication for U.S. Appl. No. 16/396,285 dated Sep. 7, 2021.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.

(56) References Cited

OTHER PUBLICATIONS

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

Winkler et al., The First Evaluation of Brain Shift During Functional Neurosurgery by Deformation Field Analysis, J. Neural. Neurosurg. Psychiatry, 76:1161-1163, Aug. 2005.

Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.

Ward, H. E., et al., "Update on deep brain stimulation for neuropsychiatric disorders," Neurobiol Dis 38 (3) (2010), pp. 346-353.

Alberts et al. "Bilateral subthalamic stimulation impairs cognitive-motor performance in Parkinson's disease patients." Brain (2008), 131, 3348-3360, Abstract.

Butson, Christopher R., et al., "Sources and effects of electrode impedance during deep brain stimulation", Clinical Neurophysiology. vol. 117.(2006),447-454.

An, et al., "Prefronlal cortical projections to longitudinal columns in the midbrain periaqueductal gray in macaque monkeys," J Comp Neural 401 (4) (1998), pp. 455-479.

Bulson, C. R., et al., "Tissue and electrode capacitance reduce neural activation volumes during deep brain stimulation," Clinical Neurophysiology, vol. 116 (2005), pp. 2490-2500.

Carmichael, S. T., et al., "Connectional networks within the orbital and medial prefronlal cortex of macaque monkeys," J Comp Neural 371 (2) (1996), pp. 179-207.

Croxson, et al., "Quantitative investigation of connections of the prefronlal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neurol 421(2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: worldwide experience," Mol Psychiatry 15 (1) (2010), pp. 64-79.

Greenberg. et al., "Three-year outcomes in deep brain stimulation for highly resistant obsessive-compulsive disorder," Neuropsychopharmacology 31 (11) (2006), pp. 2384-2393.

Cutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.

Hines, M. L., et al., "The NEURON simulation environment," Neural Comput., 9(6) (Aug. 15, 1997), pp. 1179-1209.

Hua, et al., "Tract probability maps in stereotaxic spaces: analyses of white matter anatomy and tract-specific quantification," Neuroimage 39 (1) (2008), pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 21 (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

Lujan, J.L. et al., "Automated 3-Dimensional Brain Atlas Fitting to Microelectrode Recordings from Deep Brain Stimulation Surgeries," Stereotact. Fune!. Neurosurg 87(2009), pp. 229-240.

Machado. et al., "Functional topography of the ventral striatum and anterior limb of the internal capsule determined by electrical stimulation of awake patients," Clin Neurophysiol 120 (11) (2009), pp. 1941-1948.

Malone, et al., "Deep brain stimulation of the ventral capsule/ventral striatum for treatment-resistant depression," Biol Psychiatry 65 (4) (2009), pp. 267-275.

Mayberg, H. S., et al., "Deep brain stimulation for treatment-resistant depression," Neuron, 45(5) (Mar. 3, 2005), pp. 651-660.

Mayberg, H. S., et al., "Limbic-cortical dysregulation: a proposed model of depression," J Neuropsychiatry Clin Neurosci. 9 (3) (1997), pp. 471-481.

McIntyre,C. C., et al., "Network perspectives on the mechanisms of deep brain stimulation," Neurobiol Dis 38 (3) (2010), pp. 329-337.

Miocinovic, S., et al., "Experimental and theoretical characterization of the voltage distribution generated by deep brain stimulation," Exp Neurol 216 (i) (2009), pp. 166-176.

Nuttin, et al., "Electrical stimulation in anterior limbs of internal capsules in patients with obsessive-compulsive disorder," Lancet 354 (9189) (1999), p. 1526.

Saxena, et al., "Cerebral glucose metabolism in obsessive-compulsive hoarding," Am J Psychiatry. 161 (6) (2004), pp. 1038-1048.

Viola, et al., "Importance-driven focus of attention," IEEE Trans Vis Comput Graph 12 (5) (2006), pp. 933-940.

Wakana, S., et al., "Reproducibility of quantitative tractography methods applied to cerebral white matter," Neuroimage 36 (3) (2007), pp. 630-644.

Mayr et al., "Basic Design and Construction of the Vienna FES Implants: Existing Solutions and Prospects for New Generations of Implants", Medical Engineering & Physics, 2001; 23:53-60.

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, DR., et al., "Analysis of a model for excitation of myelinated nerve," IEEE Trans Biomed Eng., vol. 23 (1976), pp. 329-337.

Micheli-Tzanakou, E., et al., "Computational Intelligence for target assesment in Parkinson's disease," Proceedings of SPIE vol. 4479, Applications and Science of Neural Networks, Fuzzy Systems, and Evolutionary Computation IV (2001), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

(56) References Cited

OTHER PUBLICATIONS

Moro, E, et al., "The impact on Parkinson's disease of electrical parameter settings in STN stimulation," Neurology, 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J Neurol. Neurosurg. Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
Si. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation: influence of collateral branching," IEEE Transactions on Biomedical Engineering, 39(9) (Sep. 1992), pp. 903-912.
Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.
Testerman, Roy L., "Coritical response to callosal stimulation: A model for determining safe and efficient stimulus parameters," Annals of Biomedical Engineering, 6(4) (1978), pp. 438-452.
Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (SuppL 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al., "Patient-specific analysis of the volume of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. Dec. 12, 1997, pp. 1210-1220.
Official Commuication for U.S. Appl. No. 16/396,285 dated Sep. 21, 2020.
Official Commuication for U.S. Appl. No. 16/396,285 dated Nov. 18, 2020.
Official Commuication for U.S. Appl. No. 16/396,285 dated Apr. 30, 2021.
Official Commuication for U.S. Appl. No. 16/396,285 dated Sep. 7, 2021.

\* cited by examiner

SYSTEMS AND METHODS FOR VISUALIZING AND PROGRAMMING ELECTRICAL STIMULATION

CROSS-REFERENCE TO RELATED APPLICATIONS

This application is a continuation of U.S. patent application Ser. No. 16/396,285, filed Apr. 26, 2019, which issued as U.S. Pat. No. 11,285,329, which claims the benefit under 35 U.S.C. § 119(e) of U.S. Provisional Patent Application Ser. No. 62/663,895, filed Apr. 27, 2018, both of which are incorporated herein by reference.

FIELD

The present disclosure is directed to the area of implantable electrical stimulation systems and methods of making and using the systems. The present disclosure is also directed to systems and methods for visualizing stimulation or for programming an electrical stimulation system.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a system for programming electrical stimulation of a patient using an implantable electrical stimulation system including an implantable pulse generator and a lead having a plurality of electrodes. The system includes a processor configured to obtain a cathodic volume of activation ("VOA') for at least one cathode, wherein the cathodic VOA is an estimated volume of tissue activated by the at least one cathode using a set of stimulation parameters; obtain an anodic VOA for at least one anode, wherein the anodic VOA is an estimated volume of tissue activated by the at least one anode using a set of stimulation parameters; and determine to display a graphical representation of the electrodes, a graphical representation of the cathodic VOA, and a graphical representation the anodic VOA. Optionally, the processor is also configured to, when the cathodic VOA or anodic VOA is modified using modification controls, modify the graphical representation of the cathodic VOA or anodic VOA and determine a modified set of stimulation parameters corresponding to the modified cathodic VOA or anodic VOA; receive direction to program the implantable pulse generator with the set of stimulation parameters or modified set of stimulation parameters; and initiate a signal that provides the implantable pulse generator of the electrical stimulation system with the selected one of the set of stimulation parameters or modified set of stimulation parameters for generating electrical stimulation for the patient through the electrodes of the lead.

Another aspect is a method for programming electrical stimulation of a patient using an implantable electrical stimulation system including an implantable pulse generator and a lead having a plurality of electrodes. The method includes obtaining a cathodic volume of activation ("VOA') for at least one cathode, wherein the cathodic VOA is an estimated volume of tissue activated by the at least one cathode using a set of stimulation parameters; obtaining an anodic VOA for at least one anode, wherein the anodic VOA is an estimated volume of tissue activated by the at least one anode using a set of stimulation parameters; and determining to display a graphical representation of the electrodes, a graphical representation of the cathodic VOA, and a graphical representation the anodic VOA. Optionally, the method also includes, when the cathodic VOA or anodic VOA is modified using modification controls, modifying the graphical representation of the cathodic VOA or anodic VOA and determining a modified set of stimulation parameters corresponding to the modified cathodic VOA or anodic VOA; receiving direction to program the implantable pulse generator with the set of stimulation parameters or modified set of stimulation parameters; and initiating a signal that provides the implantable pulse generator of the electrical stimulation system with the selected one of the set of stimulation parameters or modified set of stimulation parameters for generating electrical stimulation for the patient through the electrodes of the lead.

A further aspect is non-transitory computer-readable medium having computer executable instructions stored thereon that, when executed by a processor, cause the processor to perform the method describe above.

In at least some aspects, the processor is further configured to, or the method further includes a step to, determine to display controls for turning off the display of the graphical representation of the cathodic VOA or the graphical representation of the anodic VOA. In at least some aspects, determining to display the graphical representation of the cathodic VOA and the graphical representation of the anodic VOA includes determining to display the graphical representation of the cathodic VOA for regions that are closer to any one of the at least one cathode than to any one of the at least one anode and determining to display the graphical representation of the anodic VOA for regions that are closer to any one of the at least one anode than to any one of the at least one cathode.

In at least some aspects, determining to display the graphical representation of the cathodic VOA and the graphical representation of the anodic VOA includes using different graphical features to distinguish the graphical representation of the cathodic VOA and the graphical representation of the anodic VOA. In at least some aspects, using different graphical features includes using a third graphical feature for any region in which the cathodic VOA overlaps the anodic VOA.

In at least some aspects, the modification controls include move controls to move the cathodic VOA or anodic VOA relative to the lead. In at least some aspects, the modification controls include stretch or compress controls to stretch or compress the cathodic VOA or anodic VOA. In at least some aspects, the processor is further configured to determine to display a control for presenting an animation of a VOA for a time-varying stimulation.

In at least some aspects, obtaining the cathodic VOA includes obtaining cathodic VOAs for a plurality of different stimulation sets; obtaining the anodic VOA includes obtaining anodic VOAs for the plurality of different stimulation sets; and determining to display the graphical representation of the cathodic VOA and the graphical representation of the anodic VOA includes determining to display the cathodic VOAs as a set of contour lines and the anodic VOAs as a set of contour lines.

In at least some aspects, obtaining the cathodic VOA includes obtaining cathodic VOAs for a plurality of different stimulation sets; obtaining the anodic VOA includes obtaining anodic VOAs for the plurality of different stimulation sets; and determining to display the graphical representation of the cathodic VOA and the graphical representation of the anodic VOA includes determining to display the cathodic VOAs using a first variation in shading or color and the anodic VOAs using a second variation in shading or color.

Another aspect is a system for programming electrical stimulation of a patient using an implantable electrical stimulation system including an implantable pulse generator and a lead having a plurality of electrodes. The system includes a processor configured to obtain a fiber volume of activation ("VOA') for a set of stimulation parameters, wherein the fiber VOA is an estimated volume of tissue in which nerve fibers are activated using the set of stimulation parameters; obtain a cell VOA for a set of stimulation parameters, wherein the cell VOA is an estimated volume of tissue in which neural cells are activated using the set of stimulation parameters; and determine to display a graphical representation of the electrodes, a graphical representation of the fiber VOA, and a graphical representation the cell VOA. Optionally, the processor is further configured to, when the fiber VOA or cell VOA is modified using modification controls, modify the graphical representation of the fiber VOA or cell VOA and determine a modified set of stimulation parameters corresponding to the modified fiber VOA or cell VOA; receive direction to program the implantable pulse generator with the set of stimulation parameters or modified set of stimulation parameters; and initiate a signal that provides the implantable pulse generator of the electrical stimulation system with the set of stimulation parameters or modified set of stimulation parameters for generating electrical stimulation for the patient through the electrodes of the lead.

Yet another aspect is a method for programming electrical stimulation of a patient using an implantable electrical stimulation system including an implantable pulse generator and a lead having a plurality of electrodes. The method includes obtaining a fiber volume of activation ("VOA') for a set of stimulation parameters, wherein the fiber VOA is an estimated volume of tissue in which nerve fibers are activated using the set of stimulation parameters; obtaining a cell VOA for a set of stimulation parameters, wherein the cell VOA is an estimated volume of tissue in which neural cells are activated using the set of stimulation parameters; and determining to display a graphical representation of the electrodes, a graphical representation of the fiber VOA, and a graphical representation the cell VOA. Optionally, the method further includes, when the fiber VOA or cell VOA is modified using modification controls, modifying the graphical representation of the fiber VOA or cell VOA and determining a modified set of stimulation parameters corresponding to the modified fiber VOA or cell VOA; receiving direction to program the implantable pulse generator with the set of stimulation parameters or modified set of stimulation parameters; and initiating a signal that provides the implantable pulse generator of the electrical stimulation system with the set of stimulation parameters or modified set of stimulation parameters for generating electrical stimulation for the patient through the electrodes of the lead.

A further aspect is non-transitory computer-readable medium having computer executable instructions stored thereon that, when executed by a processor, cause the processor to perform the method describe above.

In at least some aspects, obtaining the fiber VOA includes obtaining fiber VOAs for a plurality of different stimulation sets; obtaining the cell VOA includes obtaining cell VOAs for the plurality of different stimulation sets; and determining to display the graphical representation of the fiber VOA and the graphical representation of the cell VOA includes determining to display the fiber VOAs as a set of contour lines and the cell VOAs as a set of contour lines.

In at least some aspects, obtaining the fiber VOA includes obtaining fiber VOAs for a plurality of different stimulation sets; obtaining the cell VOA includes obtaining cell VOAs for the plurality of different stimulation sets; and determining to display the graphical representation of the fiber VOA and the graphical representation of the cell VOA includes determining to display the fiber VOAs using a first variation in shading or color and the cell VOAs using a second variation in shading or color.

In at least some aspects, determining to display the graphical representation of the fiber VOA and the graphical representation of the cell VOA includes using different graphical features to distinguish the graphical representation of the fiber VOA and the graphical representation of the cell VOA. In at least some aspects, using different graphical features includes using a third graphical feature for any region in which the fiber VOA overlaps the cell VOA.

In at least some aspects, the modification controls include move controls to move the fiber VOA or cell VOA relative to the lead. In at least some aspects, the modification controls include stretch or compress controls to stretch or compress the fiber VOA or cell VOA. In at least some aspects, the processor is further configured to determine to display a control for presenting an animation of a VOA for a time-varying stimulation. In at least some aspects, the processor is further configured to, or the method further includes a step to, determine to display controls for turning off the display of the graphical representation of the fiber VOA or the graphical representation of the cell VOA. In at least some aspects, determining to display the graphical representation of the fiber VOA and the graphical representation of the cell VOA includes using different graphical features to distinguish the graphical representation of the fiber VOA and the graphical representation of the cell VOA Yet another aspect is a system for programming electrical stimulation of a patient using an implantable electrical stimulation system including an implantable pulse generator and a lead having a plurality of electrodes. The system includes a processor configured to determine which of a plurality of anatomical elements are activated by a threshold amount by cathodic stimulation or anodic stimulation using a set of stimulation parameters; and determine to display a graphical representation of the electrodes and graphical representation of the anatomical elements, indicating which of the anatomical elements are activated by a threshold amount by cathodic stimulation, which of the anatomical elements are activated by a threshold amount by anodic stimulation, and which of the anatomical elements are not activated. Optionally, the processor is further configured to, when the set of stimulation parameters is modified using modification controls, determine which of the anatomical elements are activated by a threshold amount by cathodic stimulation or anodic stimulation using the modified set of stimulation parameters and modify the graphical representations of the anatomical elements; receive direction to program the implantable pulse generator with the set of stimulation parameters or modified set of stimulation parameters; and initiate a signal that provides the implantable pulse generator of the electrical stimulation system with the set of stimulation parameters or modified set of stimulation parameters for generating electrical stimulation for the patient through the electrodes of the lead.

Another aspect is a method for programming electrical stimulation of a patient using an implantable electrical stimulation system including an implantable pulse generator and a lead having a plurality of electrodes. The method includes determining which of a plurality of anatomical elements are activated by a threshold amount by cathodic stimulation or anodic stimulation using the set of stimulation parameters; and determining to display a graphical representation of the electrodes and graphical representation of the anatomical elements, indicating which of the anatomical elements are activated by a threshold amount by cathodic stimulation, which of the anatomical elements are activated by a threshold amount by anodic stimulation, and which of the anatomical elements are not activated. Optionally, the method also includes, when the set of stimulation parameters is modified using modification controls, determining which of the anatomical elements are activated by a threshold amount by cathodic stimulation or anodic stimulation using the modified set of stimulation parameters and modifying the graphical representations of the anatomical elements; receiving direction to program the implantable pulse generator with the set of stimulation parameters or modified set of stimulation parameters; and initiating a signal that provides the implantable pulse generator of the electrical stimulation system with the set of stimulation parameters or modified set of stimulation parameters for generating electrical stimulation for the patient through the electrodes of the lead.

A further aspect is non-transitory computer-readable medium having computer executable instructions stored thereon that, when executed by a processor, cause the processor to perform the method describe above.

In at least some aspects, determining to display the graphical representation of the anatomical elements includes using different graphical features to distinguish the graphical representation of the anatomical elements activated by cathodic stimulation and the graphical representation of the anatomical elements activated by anodic stimulation.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
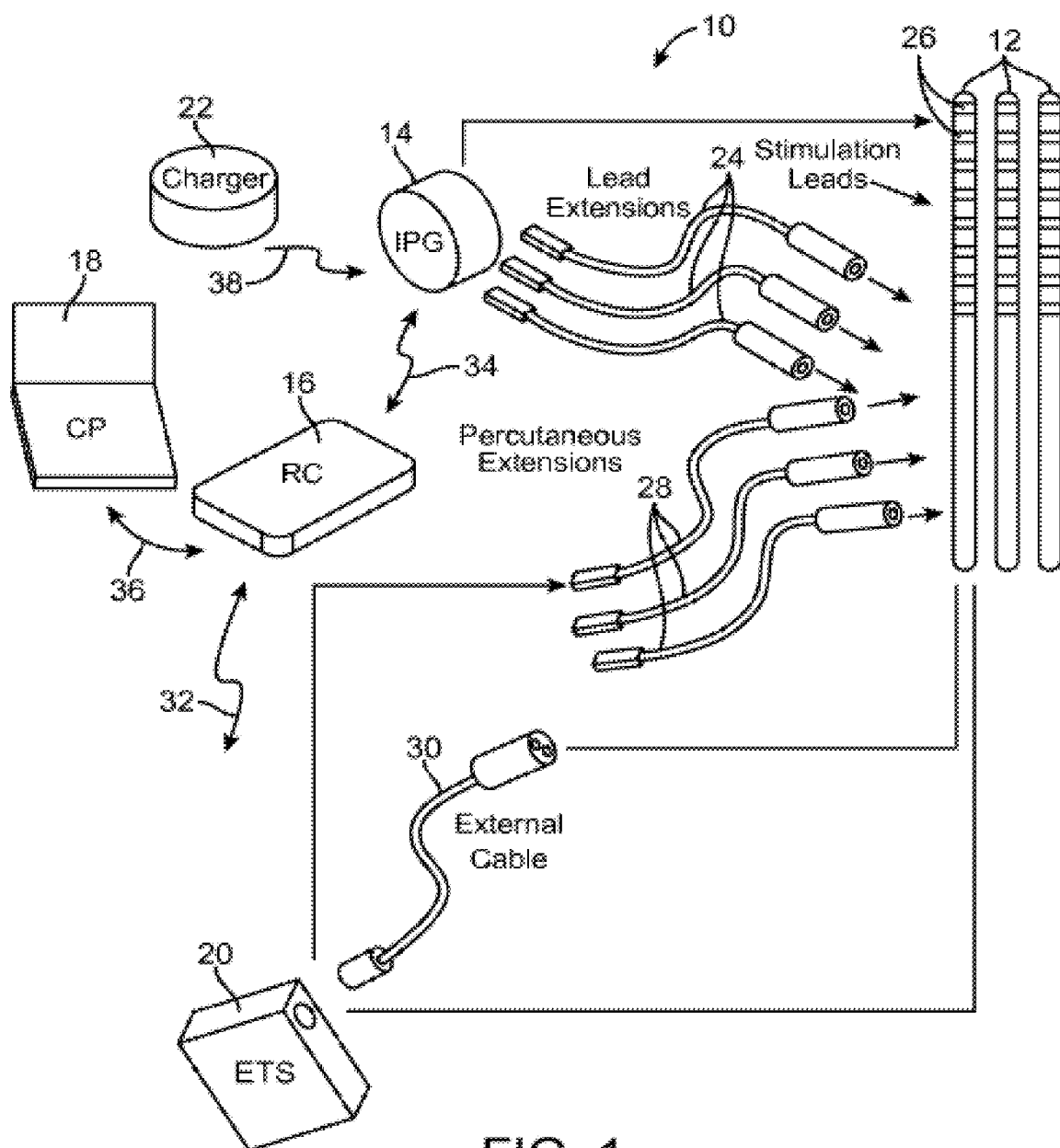
FIG. 1 is a schematic view of one embodiment of an electrical stimulation system.

The present disclosure is directed to the area of implantable electrical stimulation systems and methods of making and using the systems. The present disclosure is also directed to systems and methods for visualizing stimulation or for programming an electrical stimulation system.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain or spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves, muscles, and tissues. In particular, stimulation may stimulate specific targets. Examples of such targets include, but are not limited to, the subthalamic nucleus (STN), internal segment of the globus pallidus (GPi), external segment of the globus pallidus (GPe), and the like. In at least some embodiments, an anatomical structure is defined by its physical structure and a physiological target is defined by its functional attributes. In at least one of the various embodiments, the lead may be positioned at least partially within the target, but in other embodiments, the lead may be near, but not inside, the target.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The IPG 14 can be implanted into a patient's body, for example, below the patient's clavicle area or within the patient's buttocks or abdominal cavity. The IPG 14 can have eight stimulation channels which may be independently programmable to control the magnitude of the current stimulus from each channel. In at least some embodiments, the IPG 14 can have more or fewer than eight stimulation channels (for example, 4-, 6-, 16-, 32-, or more stimulation channels). The IPG 14 can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
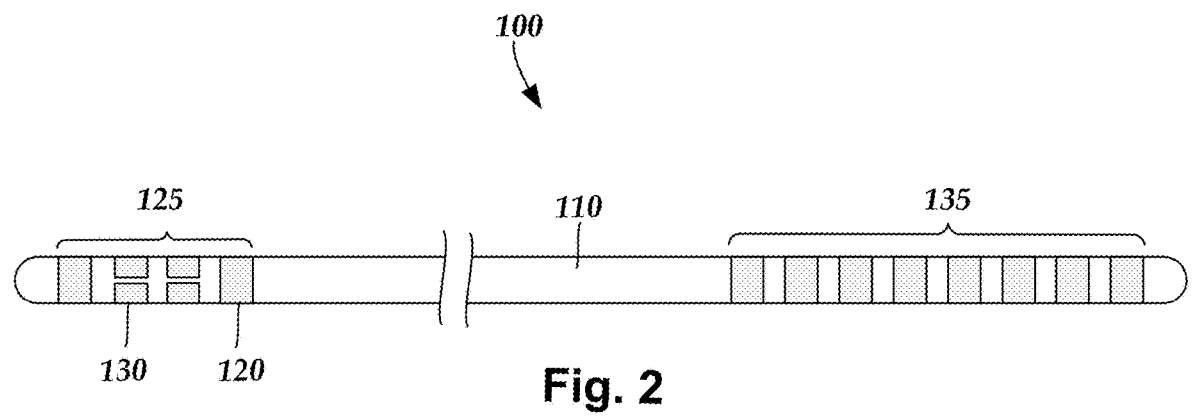
FIG. 2 is a schematic side view of one embodiment of an electrical stimulation lead.

FIG. 2 illustrates one embodiment of a lead 100 with electrodes 125 disposed at least partially about a circumference of the lead 100 along a distal end portion of the lead 100 and terminals 135 disposed along a proximal end portion of the lead 100. The lead 100 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of a stylet (not shown). The lead 100 can be guided to the target location within the brain using, for example, a stereotactic frame and a microdrive motor system. In at least some embodiments, the microdrive motor system can be fully or partially automatic. The microdrive motor system may be configured to perform one or more of the following actions (alone or in combination): insert the lead 100, advance the lead 100, retract the lead 100, or rotate the lead 100.

In at least some embodiments, measurement devices coupled to the muscles or other tissues stimulated by the target neurons, or a unit responsive to the patient or clinician, can be coupled to the IPG 14 or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 100 for deep brain stimulation can include stimulation electrodes, recording electrodes, or both. In at least some embodiments, the lead 100 is rotatable so that the stimulation electrodes can be aligned with the target neurons after the neurons have been located using the recording electrodes.

Stimulation electrodes may be disposed on the circumference of the lead 100 to stimulate the target neurons. Stimulation electrodes may be ring-shaped so that current projects from each electrode equally in every direction from the position of the electrode along a length of the lead 100. In the embodiment of FIG. 2, two of the electrodes 125 are ring electrodes 120. Ring electrodes typically do not enable stimulus current to be directed from only a limited angular range around a lead. Segmented electrodes 130, however, can be used to direct stimulus current to a selected angular range around a lead. When segmented electrodes are used in conjunction with an implantable pulse generator that delivers constant current stimulus, current steering can be achieved to more precisely deliver the stimulus to a position around an axis of a lead (i.e., radial positioning around the axis of a lead). To achieve current steering, segmented electrodes can be utilized in addition to, or as an alternative to, ring electrodes.

The lead 100 includes a lead body 110, terminals 135, one or more ring electrodes 120, and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes 125 are made of a material that is biocompatible and does not substantially corrode under expected operating conditions in the operating environment for the expected duration of use.

Each of the electrodes 125 can either be used or unused (OFF). When an electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference.

Figure 3:
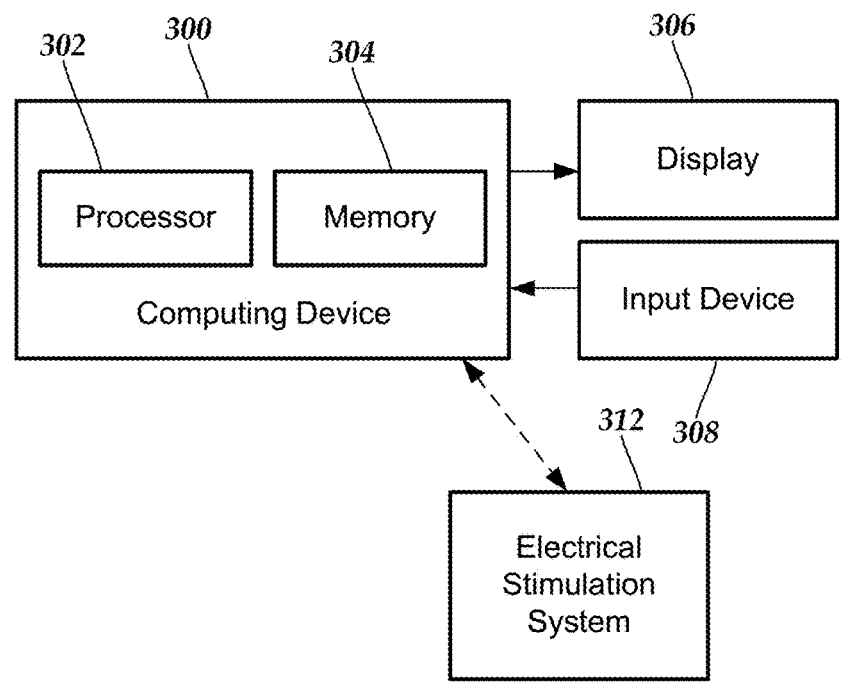
FIG. 3 is a schematic block diagram of one embodiment of a system for determining stimulation parameters.

FIG. 3 illustrates one embodiment of a system for practicing the invention. The system can include a computing device 300 or any other similar device that includes a processor 302 and a memory 304, a display 306, an input device 308, and, optionally, an electrical stimulation system 312.

The computing device 300 can be a computer, tablet, mobile device, or any other suitable device for processing information. The computing device 300 can be local to the user or can include components that are non-local to the computer including one or both of the processor 302 or memory 304 (or portions thereof). For example, in at least some embodiments, the user may operate a terminal that is connected to a non-local computing device. In other embodiments, the memory can be non-local to the user.

The computing device 300 can utilize any suitable processor 302 and the term "a processor" can include one or more hardware processors within the computing device or other components of the system or may be local to the user or non-local to the user or other components of the computing device. The processor 302 is configured to execute instructions provided to the processor 302, as described below.

Any suitable memory 304 can be used for the computing device 302. The memory 304 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 306 can be any suitable display device, such as a monitor, screen, display, or the like, and can include a printer. The input device 308 can be, for example, a keyboard, mouse, touch screen, track ball, joystick, voice recognition system, or any combination thereof, or the like.

The electrical stimulation system 312 can include, for example, any of the components illustrated in FIG. 1. The electrical stimulation system 312 may communicate with the computing device 300 through a wired or wireless connection or, alternatively or additionally, a user can provide information between the electrical stimulation system 312 and the computing device 300 using a computer-readable medium or by some other mechanism. In at least some embodiments, the computing device 300 may include part of the electrical stimulation system, such as, for example, the IPG 14, CP 18, RC 16, ETS 20, or any combination thereof.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (for example, RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

During programming sessions, as well as at other times, it can be helpful to visualize the region that will be stimulated. Stimulation region visualization systems and methods can be used to predict or estimate a region of stimulation for a given set of stimulation parameters. In at least some embodiments, the systems and methods further permit a user to modify stimulation parameters and visually observe how such modifications can change the predicted or estimated stimulation region. Such algorithms and systems may provide greater ease of use and flexibility and may enable or enhance stimulation therapy. The terms "stimulation field map" (SFM), "volume of activation" (VOA), or "volume of tissue activated (VTA)" are often used to designate an estimated region of tissue that will be stimulated for a particular set of stimulation parameters. Any suitable method for determining the VOA/SFM/VTA can be used including those described in, for example, U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; and 2015/0066111; and U.S. Provisional Patent Application Ser. No. 62/030,655, all of which are incorporated herein by reference.

Existing VOA/SFM/VTA models are generally based on neural elements, such as neural fibers, that are preferentially activated by cathodic stimulation (e.g., stimulation near a cathode). Anodic stimulation (e.g., stimulation near an anode) can activate different neural elements. Moreover, the threshold for stimulation of many neural elements is different for anodic and cathodic stimulation. As an example, U.S. Pat. No. 6,560,490, incorporated herein by reference in its entirety, demonstrates in FIGS. 1 and 2 that cathodic stimulation activates nerve fibers at much lower stimulation amplitudes than neuronal cells. In contrast, anodic stimulation activates neuronal cells at lower stimulation amplitudes than nerve fibers.

Because anodic stimulation activates neural elements differently from cathodic stimulation, VOA/SFM/VTA models for cathodic stimulation will likely be inaccurate in estimating the effect of anodic stimulation. For a lead producing anodic stimulation or a combination of anodic and cathodic stimulation, it can be helpful to provide a system that displays visualization of the anodic and cathodic stimulation regions and conveys to a user which type of stimulation is being visualized. Alternatively, the visualization can be by neural element type, such as nerve fiber or neural cell or any other suitable selection of neural element type.

In many instances, for monopolar cathodic stimulation, the anode of the electrical stimulation system is located on the case of the implantable pulse generator or at another site relatively distant from the cathode or cathodes on the lead. Monopolar cathodic stimulation may also include instances where the anode is distributed over a large number of (for example, at least four, five, six, seven, or more) electrodes on the lead or where the anode is positioned on the lead at a substantial distance away from the cathode (for example, the anode is near the proximal end of the array of electrodes and the cathode is near the proximal end of the electrodes.) Similarly, monopolar anodic stimulation may include instances where the cathode of the electrical stimulation system is located on the case of the implantable pulse generator or at another site relatively distant from the anode or anodes on the lead or instances where the cathode is distributed over a large number of (for example, at least four, five, six, seven, or more) electrodes on the lead or where the cathode is positioned on the lead at a substantial distance away from the anode (for example, the anode is near the proximal end of the array of electrodes and the cathode is near the proximal end of the electrodes.) Another method for identifying the anodic or cathodic nature of stimulation can be found in U.S. Pat. No. 8,190,250, incorporated herein by reference in its entirety, which observes the angle of an electric field at particular points with respect to the lead.

User interfaces can be provided to visualize anodic or cathodic stimulation or stimulation of nerve fibers, neural cells, or other neural elements. Such user interfaces can be provided on the system illustrated in FIG. 3, the CP 18 or RC 16 of FIG. 1, or any other suitable system or device.

Figure 4:
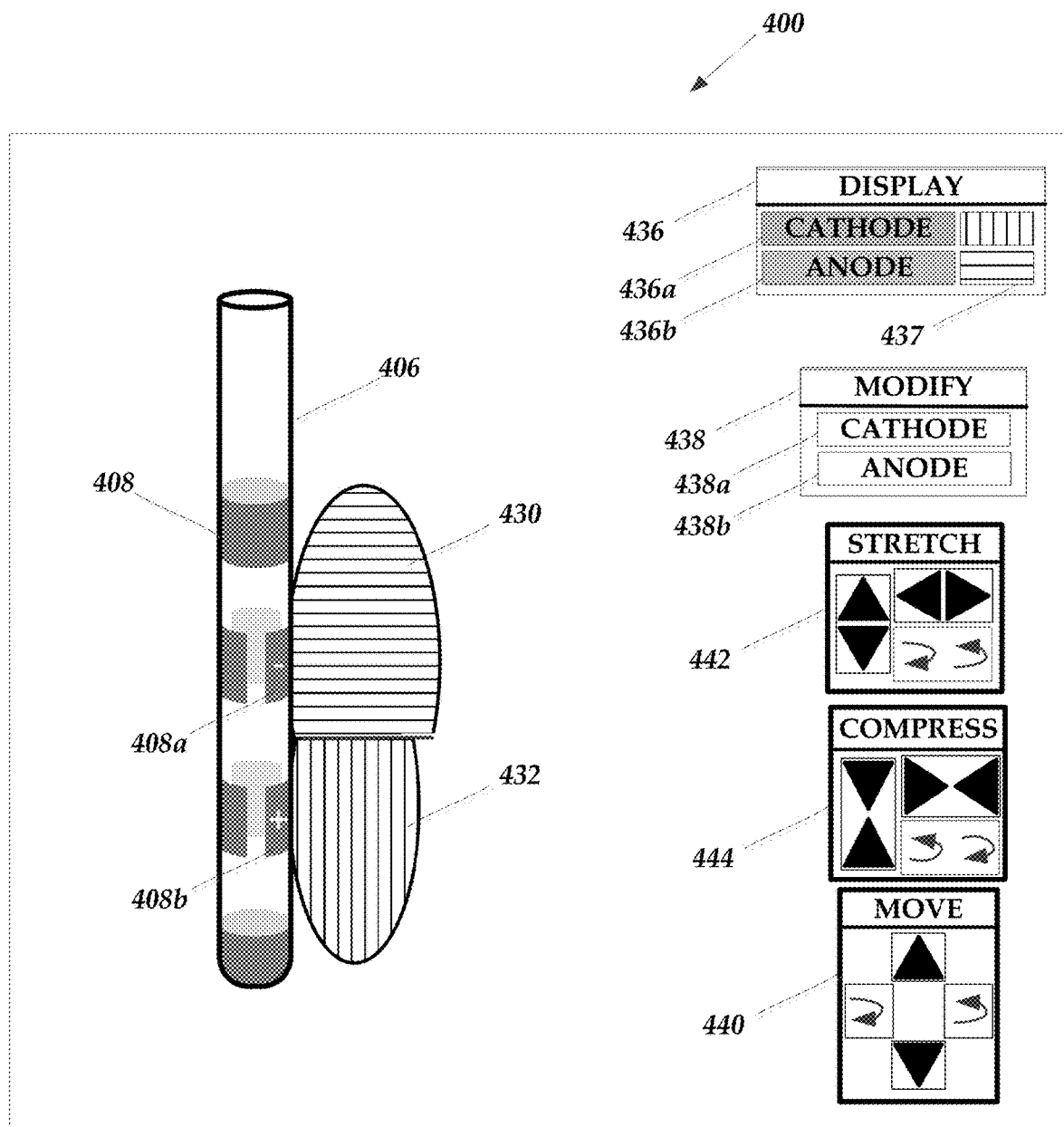
FIG. 4 is one embodiment of a user interface for visualizing cathodic and anodic stimulation.

FIG. 4 illustrates one embodiment of a user interface 400 for visualizing stimulation or for programming an electrical stimulation system. The user interface 400 includes a representation of a portion of the lead 406 with electrodes 408. In the illustrated example, electrode 408a is a cathode and electrode 408b is an anode. It will be understood that any other electrode, or combination of electrodes, could be selected to be a cathode or anode. It will also be understood that in some embodiments, either the cathode or anode may be selected to be an electrode that is distant from the illustrated portion of the lead (for example, the housing of the implantable pulse generator.)

In FIG. 4, an estimated cathodic VOA (or VTA or SFM) 430 and an estimated anodic VOA (or VTA or SFM) 432 are illustrated. The lead 406, cathodic VOA 430, and anodic VOA 432 in the user interface 400 are illustrated in two dimensions. It will be understood, however, that these objects and VOAs are three-dimensional and, in some embodiments, may be displayed three-dimensionally or using perspective display techniques. In at least some embodiments, the user interface 400 can include controls for rotating the lead 406 and VOAs 430, 432 to show these elements at different angles.

In the illustrated embodiment, the cathodic VOA 430 and anodic VOA are distinguished using different types of cross-hatching. Other methods of distinguishing the VOAs 430, 432 can be used in combination with, or as an alternative to, cross-hatching including, but not limited to, different colors, different shading, different symbols, or the like, or any combination thereof. A legend 437 for the VOAs 430, 432 may be provided.

In this embodiment, the anodic VOA 432 is illustrated in regions or at points where the nearest active electrode is an anode and the cathodic VOA 430 is illustrated in regions or at points where the nearest active electrode is a cathode. In the illustrated embodiment, there is one anode and one cathode. In other instances, there may be more than one anode or cathode. In such instances, the anodic or cathodic VOA corresponding to the nearest anode or cathode will be displayed for each particular region or point. When there are multiple anodes or cathodes, in at least some embodiments, the anodic VOA 432 will represent all of the anodes and the cathodic VOA 430 will represent all of the cathodes. In other embodiments, a different anodic VOA 432 may be presented for each of the anodes (or a subset of the anodes) and a different cathodic CTA 430 may be presented for each of the cathodes (or a subset of the cathodes). In such circumstances, the legend 437 and controls 436, 438 for selecting which VOA to display modify, described below, may include individual controls for each of the different anodic and cathodic VOAs.

In this embodiment, the distances to the active electrodes (e.g., anode and cathode) serve as a proxy for identifying which type of stimulation (anodic or cathodic) will be primarily present in a particular region or point. In other embodiments, other proxies may be used to determine whether the anodic VOA or cathodic VOA will be displayed. For example, the distances may be weighted according to type of stimulation (for example, cathodic stimulation may be weighted more heavily than anodic stimulation if cathodic stimulation is more effective for a given stimulation amplitude), type of neural elements (for example, some tissue may be more receptive to cathodic stimulation than anodic stimulation), stimulation amplitude (for example, stimulation using multiple anodes or cathodes may result in different stimulation amplitudes for the active electrodes), or the like or any combination thereof. In such embodiments, the anodic VOA 432 is displayed for regions or points where the weighted distance to the anode is greater than the weighted distance to the cathode and the cathodic VOA 430 is displayed for regions or points where the weighted distance to the cathode is greater than the weighted distance to the anode.

In other embodiments, as an alternative to, or in addition to, weighting, the proxy may be a non-linear function of the distance (for example, a function of the distance squared or the square root of the distance or a polynomial equation with the distance as a variable.)

The user interface 400 also includes one or more display controls 436 for turning the display of the cathodic VOA 430 and anodic VOA 432 on or off. In the illustrated embodiment, both the cathodic VOA 430 and anodic VOA 432 are displayed. Operation of the cathodic display control 436a can remove display of the cathodic VOA 430. Similarly, operation of the anodic display control 436b can remove display of the anodic VOA 432. In some embodiments, when one of the VOAs is removed, the other VOA remains, as illustrated in FIG. 4, limited to the region nearest the corresponding electrode. In other embodiments, when one of the VOAs is removed, the other VOA may be altered to show the entire shape of the VOA rather than being limited by the distances to the electrodes.

In at least some embodiments, the user interface 400 may include controls for modifying the VOAs 430, 432. Such controls can include a selection control 438 with individual controls 438a, 438b for selecting the cathodic VOA or anodic VOA. The controls can include move controls 440 to move the selected VOA up or down the lead or around the lead clockwise or counter-clockwise. The controls can include stretch controls 442 for stretching the selected VOA up or down the lead, away from the lead, or around the lead in the clockwise or counter-clockwise direction. The controls can include compress controls 442 for compressing the selected VOA up or down the lead, toward from the lead, or inward from the clockwise or counter-clockwise direction. Any other suitable modification controls can be included in the user interface.

In at least some embodiments, the system will determine, based on the modified VOA, changes to the stimulation parameters to approximate the modified VOA. Such changes may include, for example, changing the electrode selection or the stimulation amplitude. As an example, moving or stretching the VOA up or down the lead may include shifting some or all of the stimulation to another electrode (or electrodes) further up or down the lead. As another example, stretching the VOA away from the lead may include increasing the stimulation amplitude.

Figure 5:
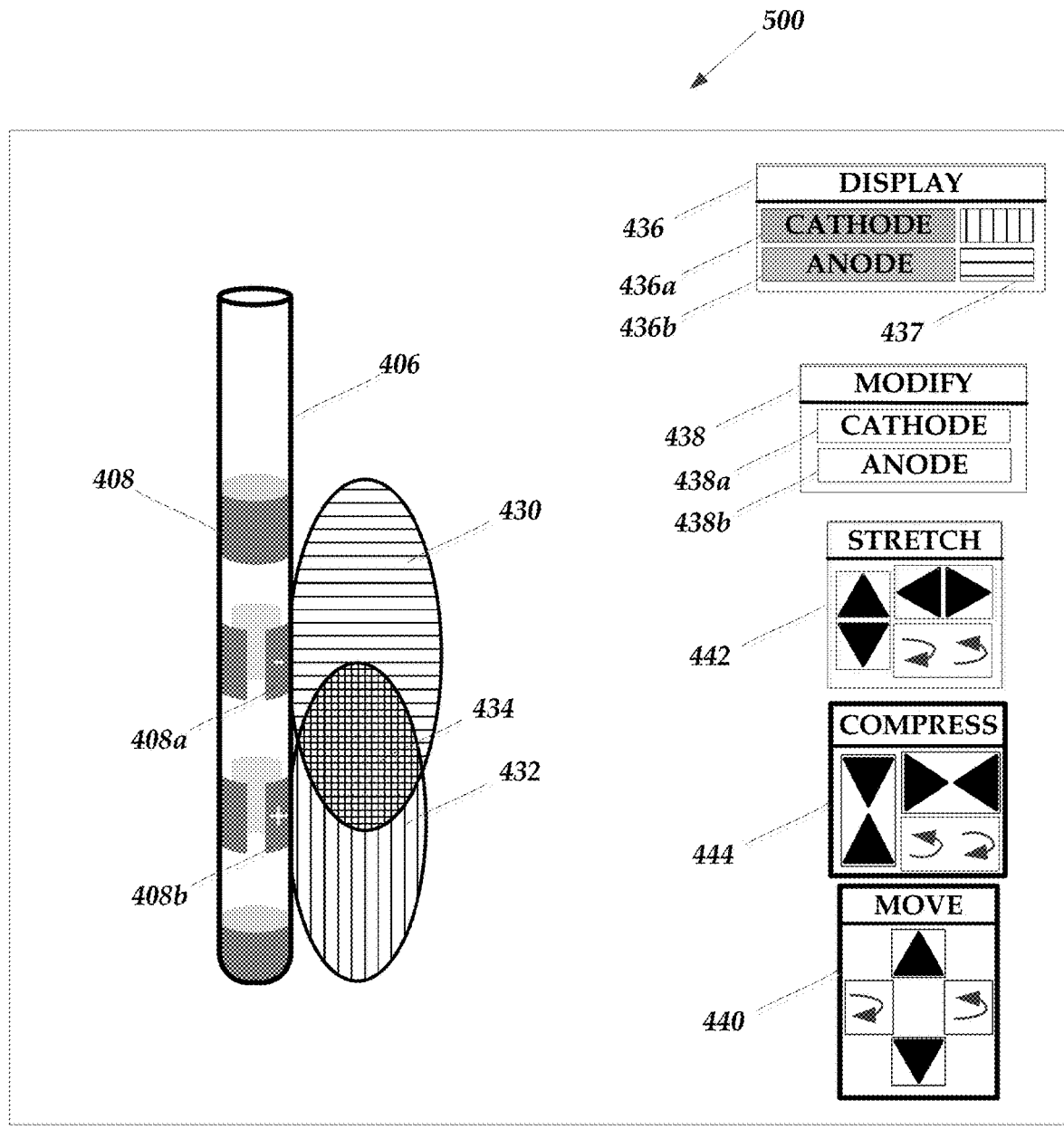
FIG. 5 is another embodiment of a user interface for visualizing cathodic and anodic stimulation.

FIG. 5 illustrates another embodiment of a user interface 500 for visualizing stimulation or for programming an electrical stimulation system. The user interface 500 includes a representation of a portion of the lead 406 with electrodes 408. In the illustrated example, electrode 408a is a cathode and electrode 408b is an anode. In FIG. 5, an estimated cathodic VOA 430 and an estimated anodic VOA 432 are illustrated including a region 434 where the cathodic VOA 430 and the anodic VOA 432 overlap. The user interface also includes the display controls 436, selection control 438, move controls 440, stretch controls 442, and compress controls 444 described above.

Figure 6:
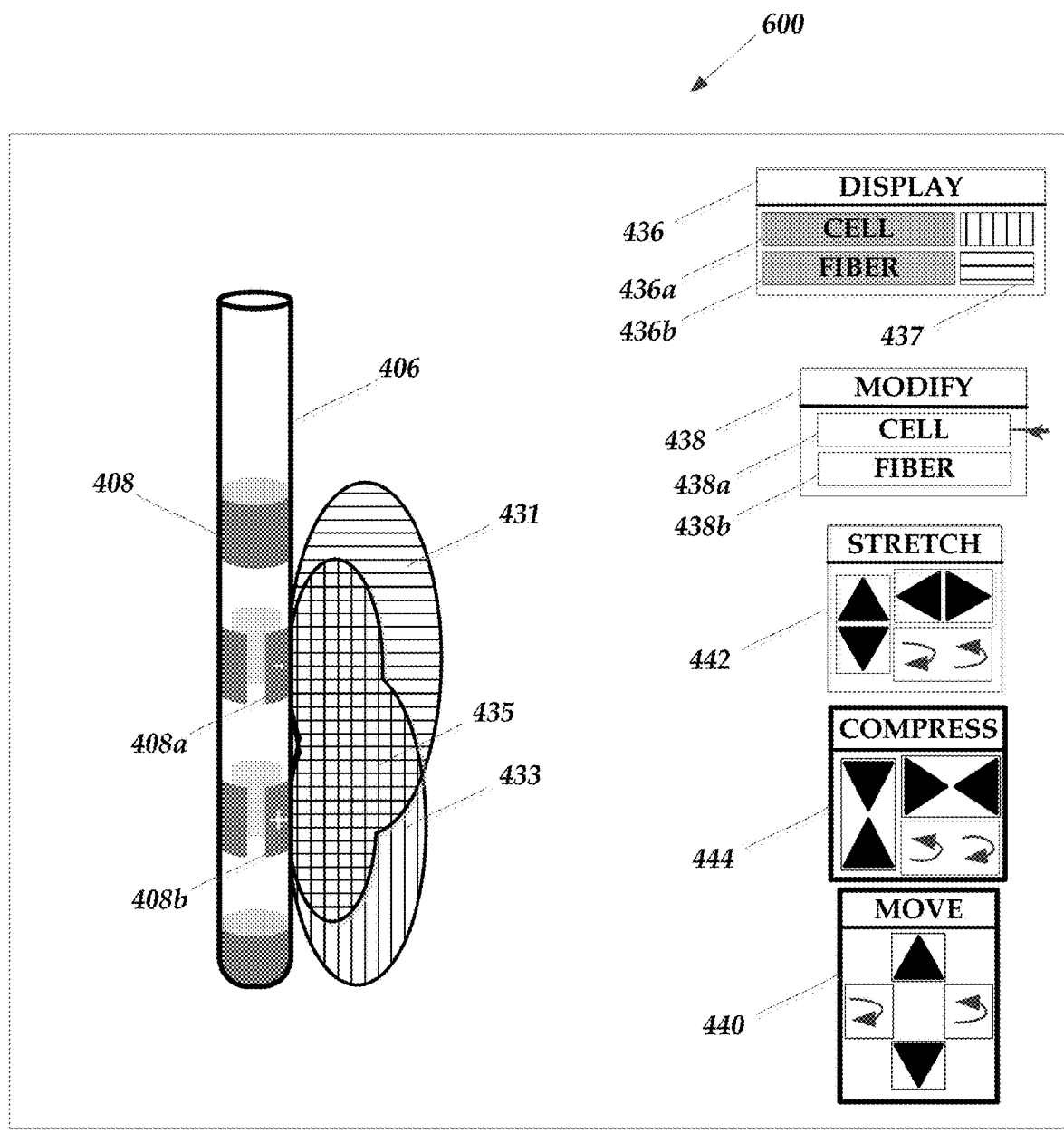
FIG. 6 is one embodiment of a user interface for visualizing fiber and cell stimulation.

FIG. 6 illustrates another embodiment of a user interface 600 for visualizing stimulation or for programming an electrical stimulation system. The user interface 600 includes a representation of a portion of the lead 406 with electrodes 408. In the illustrated example, electrode 408a is a cathode and electrode 408b is an anode. In FIG. 6, an estimated fiber VOA 431 and an estimated cell VOA 433 are illustrated including a region 435 where the fiber VOA 431 and the cell VOA 433 overlap. As discussed above, it is found that cathodic stimulation preferentially stimulates fibers, but does provide some stimulation of neural cells. Conversely, anodic stimulation preferentially stimulates neural cells, but also stimulates fibers. Accordingly, the combination of anodic and cathodic stimulation will stimulate both fibers and neural cells, but in different and overlapping regions. In at least some embodiments, the determination of the fiber VOA 431 is at least partially based on a second difference of the scalar potential (for example, an activating function, derivative of the E field, or derivative of the J field.) In at least some embodiments, the determination of the cell VOA 433 is at least partially based on a first difference of the scalar potential (e.g., the E field or the J field.)

In other embodiments, similar to the user interface of FIG. 6, different types of neural elements can be selected for displayable VOAs. For example, large fibers, small fibers, fibers or cells oriented parallel to the lead, fibers or cells oriented perpendicular to the lead, fibers or cells oriented in a particular angular range relative to the lead, specific types of neural cells, neuron terminals, synapses, neurons with different biophysical properties (such as specific ion channel properties), or the like, or any combination thereof. In at least some embodiments, the user interface can display VOAs for two, three, four, or more different types of neural elements. In at least some embodiments, the VOAs can be determined using monopolar cathodic stimulation, monopolar anodic stimulation, or bipolar/multipolar stimulation.

The user interface also includes the display controls 436, selection control 438, move controls 440, stretch controls 442, and compress controls 444 described above. These controls, however, are now directed to displaying or modifying the fiber VOA 431 or cell VOA 433.

Figure 7:
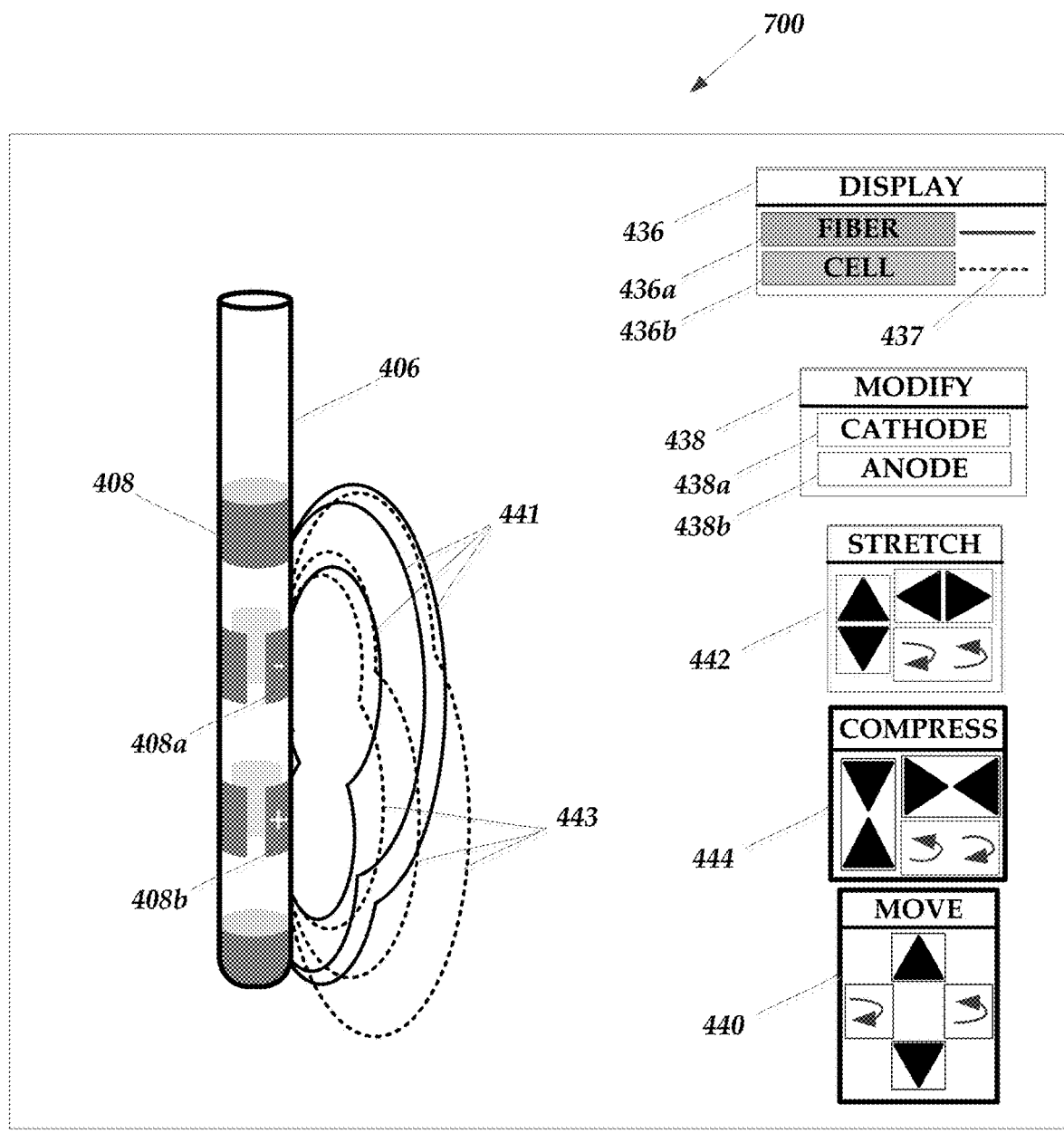
FIG. 7 is another embodiment of a user interface for visualizing fiber and cell stimulation.

FIG. 7 illustrates another embodiment of a user interface 700 for visualizing stimulation or for programming an electrical stimulation system. The user interface 700 includes a representation of a portion of the lead 406 with electrodes 408. In the illustrated example, electrode 408a is a cathode and electrode 408b is an anode. In FIG. 7, a set of estimated fiber VOA contour lines 441 and a set of estimated cell VOA contour lines 443. In another embodiment, contour lines for anodic and cathodic VOAs (see, FIGS. 4 and 5) can be displayed. Each contour line of a set corresponds to a different stimulation amplitude. In other embodiments, the contour lines can correspond to changing other stimulation parameters, such as electrode selection, pulse width, pulse duration, or the like, or any combination thereof. In another embodiment, instead of contour lines, a map of the region around the lead can be displayed with shading or coloring that varies according to the stimulation amplitude that is needed to stimulate the region. For example, shading can be darkest for lower amplitude and become lighter for higher amplitude or coloring can range from blue for lower amplitude to red for higher amplitude.

The user interface also includes the display controls 436, selection control 438, move controls 440, stretch controls 442, and compress controls 444 described above. These controls, however, are now directed to displaying or modifying the fiber VOA contour lines 441 or cell VOA contour lines 443.

Figure 8:
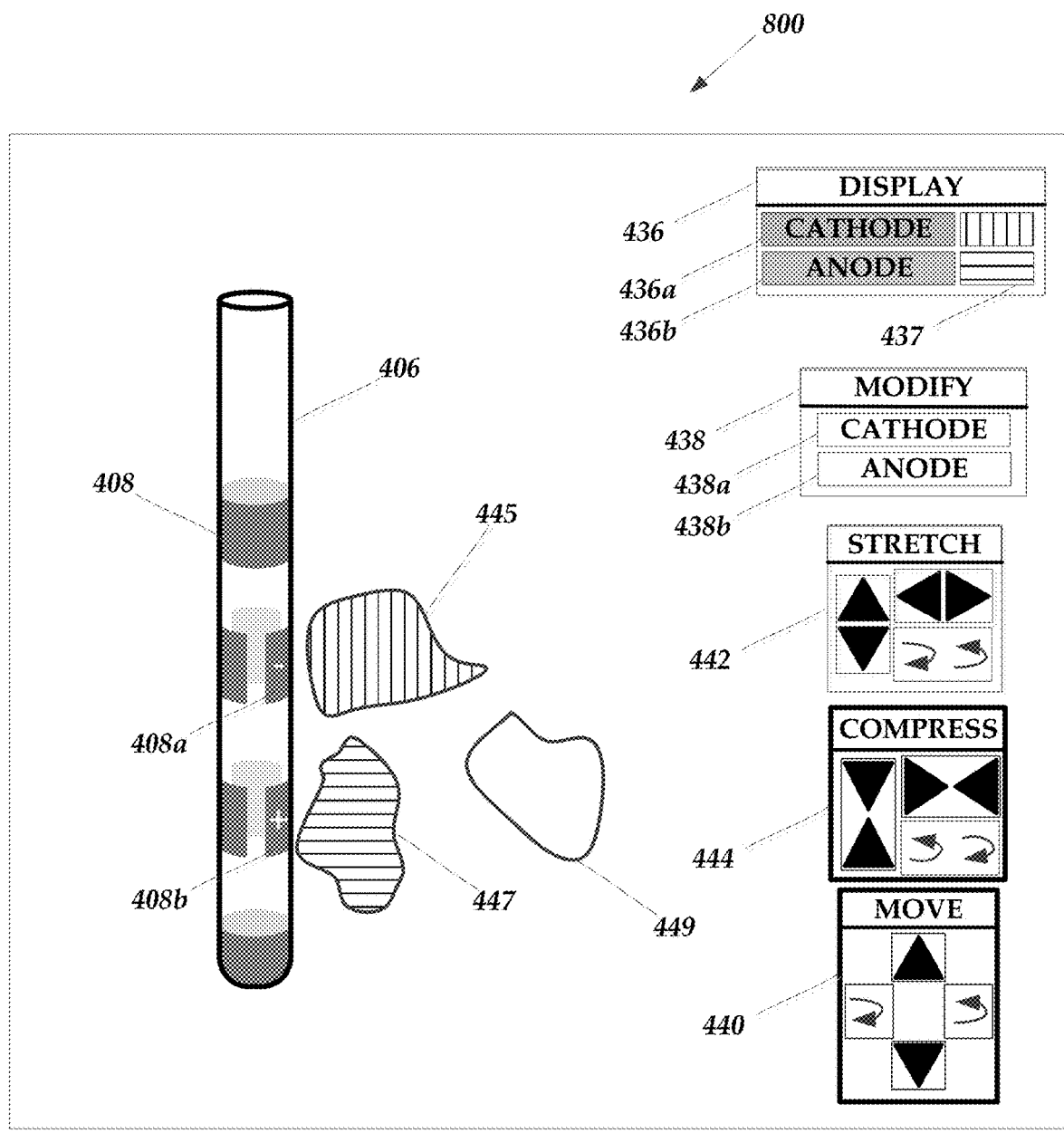
FIG. 8 is one embodiment of a user interface for visualizing anatomical element stimulation.

FIG. 8 illustrates another embodiment of a user interface 800 for visualizing stimulation or for programming an electrical stimulation system. The user interface 800 includes a representation of a portion of the lead 406 with electrodes 408. In the illustrated example, electrode 408a is a cathode and electrode 408b is an anode. In FIG. 8, instead of illustrating VOAs, anatomical elements (such as previously identified anatomical structures) are illustrated and are marked based on whether a threshold amount of the particular anatomical element is stimulated by the anode or cathode or not stimulated. In the illustrated embodiments, anatomical element 445 is stimulated by the cathode, anatomical element 447 is stimulated by the anode, and anatomical element is not stimulated. In at least some embodiments, the amount of an anatomical structure that is stimulated is determined using the VOAs described above. In at least some embodiments, a user can set the threshold amount for all anatomical elements. In at least some embodiments, a user can set the threshold amount individually for each anatomical element or subset of anatomical elements.

The user interface also includes the display controls 436, selection control 438, move controls 440, stretch controls 442, and compress controls 444 described above.

When the display or modify controls are operated, the markings on the anatomical elements will be modified based on the modifications to the cathode or anode VOAs.

In at least some embodiments, any combination of the VOAs and other elements described above for the interfaces illustrated in FIGS. 4 to 8 can be used. In at least some embodiments, multiple VOAs determined using different stimulation conditions or different types of stimulation can be used. For example, any combination of cathodic VOAs, anodic VOAs, fiber VOAs, cell VOAs, terminal VOAs, or the like can be displayed simultaneously or sequentially. Providing these different VOAs can allow a user to compare the stimulation for different conditions. In at least some embodiments, a current, most recent, or user-selected VOA may be highlighted (using, for example, a different color, bold colors or boundaries or contour lines, or shading).

In at least some embodiments, the user can select a time varying stimulation (for example, stimulation that varies from cathodic to anodic stimulation). Any of the user interfaces described above may include controls for defining the time variation. Any of the user interfaces described above may also include controls that provide an animation of the resulting time-varying VOA. For example, an animated time-varying VOA may transition from anodic to cathodic stimulation (or vice versa). The location of the time-varying VOA may remain constant or may shift over time.

Figure 9:
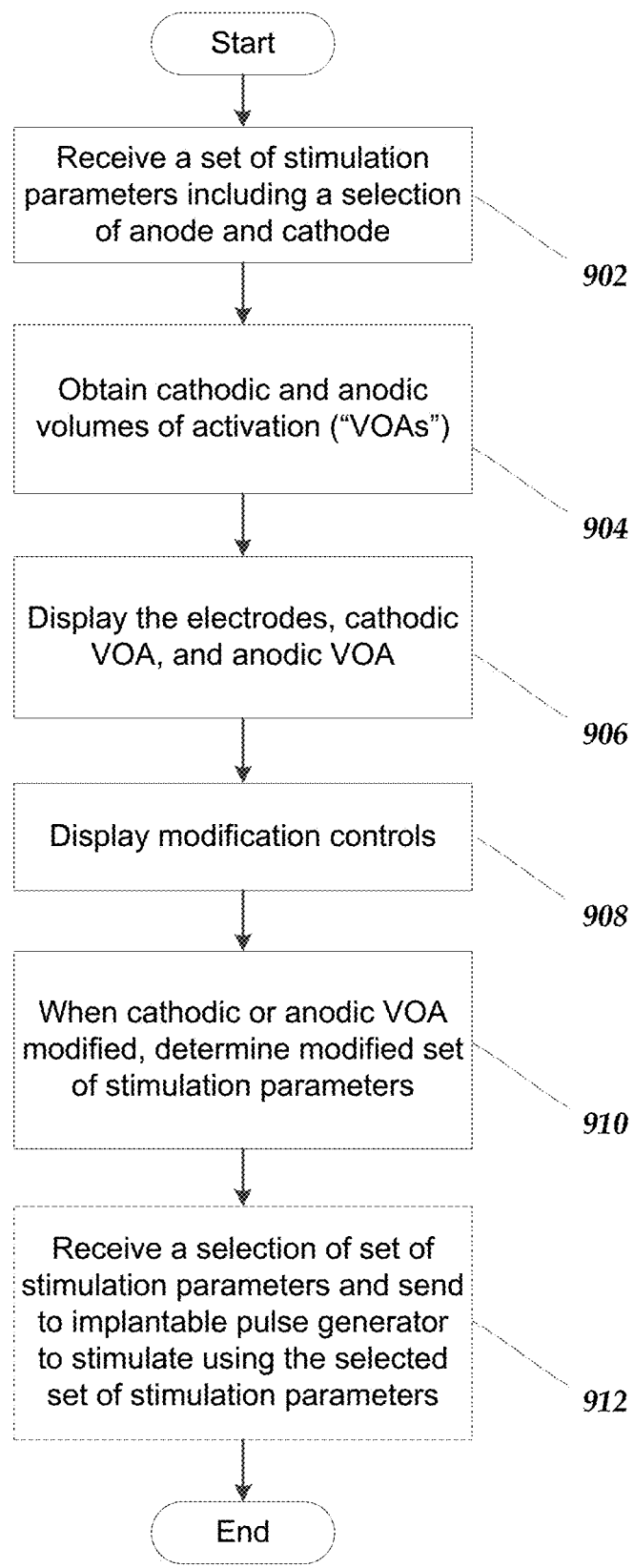
FIG. 9 is a flowchart of a first embodiment of a method of visualizing stimulation or for programming an electrical stimulation system.

FIG. 9 is a flowchart of one embodiment of a method of visualizing stimulation or for programming an electrical stimulation system. In step 902, a set of stimulation parameters is received including a selection of at least one anode and at least one cathode. In step 904, cathodic and anodic VOAs are obtained. The system may calculate the VOAs or may receive the VOAs from another system or may determine the VOAs from look-up tables, databases, or the like or may obtain the VOAs in any other suitable manner.

In step 906, the system displays the electrodes, cathodic VOA, and anodic VOA. For example, any of the user interfaces described above (including, but not limited to the user interfaces illustrated in FIGS. 4 and 5) can be used for displaying these elements. In step 908, modification controls, such as those illustrated in FIGS. 4 and 5, are displayed. In step 910, when the cathodic or anodic VOA is modified using the modification controls, the system determines a modified set of stimulation parameters that will approximate the modified VOA. In optional step 912, a selection of one set of stimulation parameters is received and the system sends the selected set of stimulation parameters to an implantable pulse generator (or other device) to provide stimulation to a patient using the selected stimulation parameters.

Figure 10:
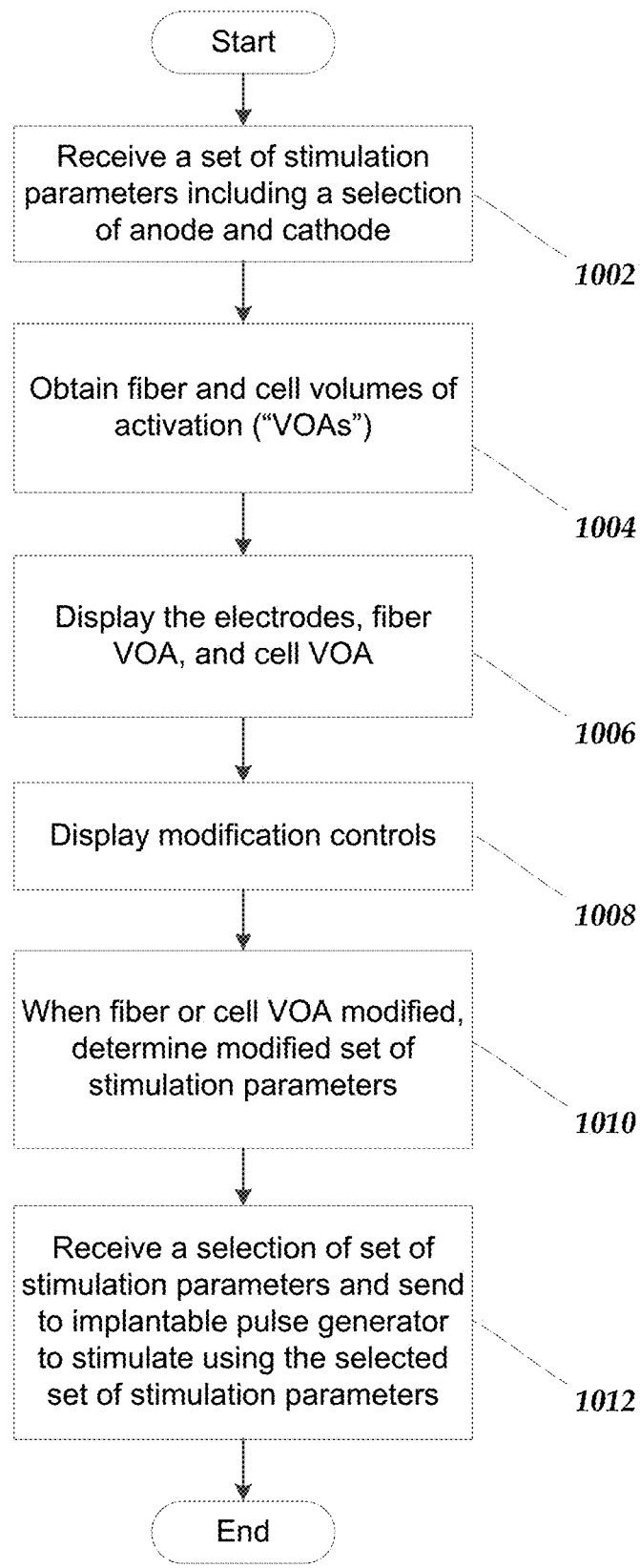
FIG. 10 is a flowchart of a second embodiment of a method of visualizing stimulation or for programming an electrical stimulation system.

FIG. 10 is a flowchart of another embodiment of a method of visualizing stimulation or for programming an electrical stimulation system. In step 1002, a set of stimulation parameters is received including a selection of at least one anode and at least one cathode. In step 1004, fiber and cell VOAs are obtained. The system may calculate the VOAs or may receive the VOAs from another system or may determine the VOAs from look-up tables, databases, or the like or may obtain the VOAs in any other suitable manner.

In step 1006, the system displays the electrodes, fiber VOA, and cell VOA. For example, any of the user interfaces described above (including, but not limited to the user interfaces illustrated in FIGS. 6 and 7) can be used for displaying these elements. In step 1008, modification controls, such as those illustrated in FIGS. 6 and 7, are displayed. In step 1010, when the fiber or cell VOA is modified using the modification controls, the system determines a modified set of stimulation parameters that will approximate the modified VOA. In optional step 1012, a selection of one set of stimulation parameters is received and the system sends the selected set of stimulation parameters to an implantable pulse generator (or other device) to provide stimulation to a patient using the selected stimulation parameters.

Figure 11:
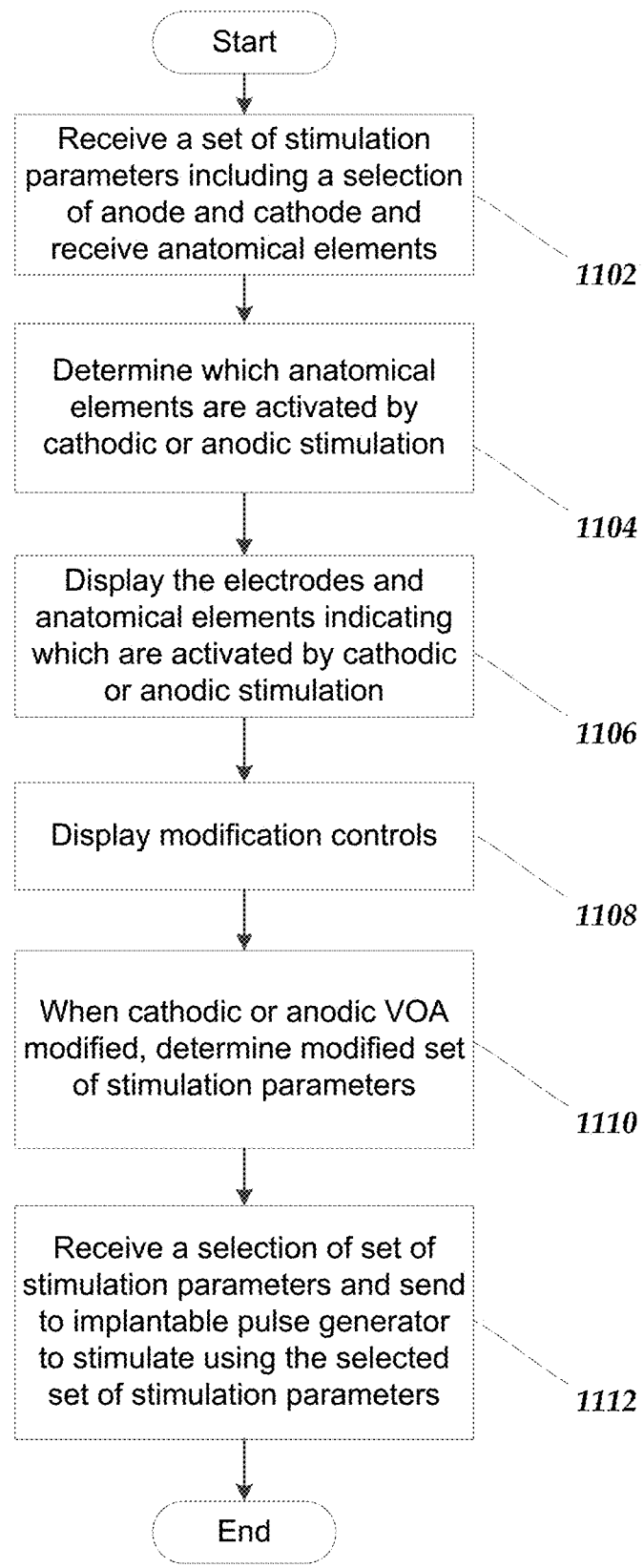
FIG. 11 is a flowchart of a third embodiment of a method of visualizing stimulation or for programming an electrical stimulation system.

FIG. 11 is a flowchart of one embodiment of a method of visualizing stimulation or for programming an electrical stimulation system. In step 1102, a set of stimulation parameters is received including a selection of at least one anode and at least one cathode. Also, a set of anatomical elements is received. In step 1104, the system determines which of the anatomical elements are stimulated, by a threshold amount, by cathodic or anodic stimulation. For example, the system may obtain the cathodic and anodic VOAs and determine which of the anatomical elements have a threshold amount within the respective VOAs.

In step 1106, the system displays the electrodes and anatomical elements indicating which of the anatomical elements are activated by a threshold amount by cathodic stimulation, which of the anatomical elements are activated by a threshold amount by anodic stimulation, and which of the anatomical elements are not activated. For example, any of the user interfaces described above (including, but not limited to the user interface illustrated in FIG. 8) can be used for displaying these elements. In step 1108, modification controls, such as those illustrated in FIG. 8, are displayed. In step 1110, when the cathodic or anodic VOA is modified using the modification controls, the system determines a modified set of stimulation parameters that will approximate the modified VOA. In optional step 1112, a selection of one set of stimulation parameters is received and the system sends the selected set of stimulation parameters to an implantable pulse generator (or other device) to provide stimulation to a patient using the selected stimulation parameters.

It will be understood that the system can include one or more of the methods described hereinabove with respect to FIGS. 9-11 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A method for programming electrical stimulation of a patient using an implantable electrical stimulation system including an implantable pulse generator and a lead having a plurality of electrodes, the method comprising:
   obtaining a cathodic volume of activation ("VOA") for monopolar cathodic stimulation using at least one cathode, wherein the cathodic VOA is an estimated volume of tissue activated by the at least one cathode using a set of stimulation parameters;
   obtaining an anodic VOA for monopolar anodic stimulation using at least one anode, wherein the anodic VOA is an estimated volume of tissue activated by the at least one anode using the set of stimulation parameters;
   displaying, on a display, a graphical representation of the plurality of electrodes, a graphical representation of the cathodic VOA, and a graphical representation of the anodic VOA;
   when the cathodic VOA or anodic VOA is modified using modification controls, modifying the graphical representation of the cathodic VOA or the graphical representation of the anodic VOA and determining a modified set of stimulation parameters corresponding to the modified graphical representation of the cathodic VOA or the modified graphical representation of the anodic VOA;
   programming the implantable pulse generator with the set of stimulation parameters or the modified set of stimulation parameters; and
   electrically stimulating the patient according to the set of stimulation parameters or the modified set of stimulation parameters using the implantable pulse generator and the plurality of electrodes of the lead.

2. The method of claim 1, further comprising displaying controls, on the display, for turning off the displaying of the graphical representation of the cathodic VOA or the graphical representation of the anodic VOA.

3. The method of claim 1, wherein displaying the graphical representation of the cathodic VOA and the graphical representation of the anodic VOA comprises displaying, on the display, the graphical representation of the cathodic VOA for regions that are closer to any one of the at least one cathode than to any one of the at least one anode and displaying, on the display, the graphical representation of the anodic VOA for regions that are closer to any one of the at least one anode than to any one of the at least one cathode.

4. The method of claim 1, wherein displaying the graphical representation of the cathodic VOA and the graphical representation of the anodic VOA comprises using different graphical features to distinguish the graphical representation of the cathodic VOA and the graphical representation of the anodic VOA.

5. The method of claim 4, wherein using different graphical features comprises using a third graphical feature for any region in which the cathodic VOA overlaps the anodic VOA.

6. The method of claim 1, wherein the modification controls comprise move, stretch, or compress controls to move, stretch, or compress the cathodic VOA or the anodic VOA relative to the lead.

7. The method of claim 1, further comprising displaying, on the display, a control for presenting an animation of the cathodic VOA or the anodic VOA for a time-varying stimulation.

8. The method of claim 1, wherein
obtaining the cathodic VOA comprises obtaining cathodic VOAs for monopolar cathodic stimulation using a plurality of different sets of stimulation parameters;
obtaining the anodic VOA comprises obtaining anodic VOAs for monopolar anodic stimulation using the plurality of different sets of stimulation parameters; and
displaying the graphical representation of the cathodic VOA and the graphical representation of the anodic VOA comprises displaying, on the display, the graphical representations of the cathodic VOAs as a set of contour lines and the graphical representations of the anodic VOAs as a set of contour lines.

9. The method of claim 1, wherein
obtaining the cathodic VOA comprises obtaining cathodic VOAs for monopolar cathodic stimulation using a plurality of different sets of stimulation parameters;
obtaining the anodic VOA comprises obtaining anodic VOAs for monopolar anodic stimulation using the plurality of different sets of stimulation parameters; and
displaying the graphical representation of the cathodic VOA and the graphical representation of the anodic VOA comprises displaying, on the display, the graphical representations of the cathodic VOAs using a first variation in shading or color and the graphical representations of the anodic VOAs using a second variation in shading or color.

10. A non-transitory computer-readable medium having computer executable instructions stored thereon that, when executed by a processor, cause the processor to perform actions for programming electrical stimulation of a patient using an implantable electrical stimulation system including an implantable pulse generator and a lead having a plurality of electrodes, the actions comprising:
obtaining a cathodic volume of activation ("VOA") for monopolar cathodic stimulation using at least one cathode, wherein the cathodic VOA is an estimated volume of tissue activated by the at least one cathode using a set of stimulation parameters;
obtaining an anodic VOA for monopolar anodic stimulation using at least one anode, wherein the anodic VOA is an estimated volume of tissue activated by the at least one anode using the set of stimulation parameters;
displaying, on a display, a graphical representation of the plurality of electrodes, a graphical representation of the cathodic VOA, and a graphical representation of the anodic VOA;
when the cathodic VOA or anodic VOA is modified using modification controls, modifying the graphical representation of the cathodic VOA or the graphical representation of the anodic VOA and determining a modified set of stimulation parameters corresponding to the modified graphical representation of the cathodic VOA or the modified graphical representation of the anodic VOA; and
initiating a signal that provides the implantable pulse generator of the electrical stimulation system with the set of stimulation parameters or the modified set of stimulation parameters for generating electrical stimulation for the patient through the plurality of electrodes of the lead.

11. The non-transitory computer-readable medium of claim 10, the actions further comprising displaying controls, on the display, for turning off the displaying of the graphical representation of the cathodic VOA or the graphical representation of the anodic VOA.

12. The non-transitory computer-readable medium of claim 10, wherein displaying the graphical representation of the cathodic VOA and the graphical representation of the anodic VOA comprises displaying, on the display, the graphical representation of the cathodic VOA for regions that are closer to any one of the at least one cathode than to any one of the at least one anode and displaying, on the display, the graphical representation of the anodic VOA for regions that are closer to any one of the at least one anode than to any one of the at least one cathode.

13. The non-transitory computer-readable medium of claim 10, wherein displaying the graphical representation of the cathodic VOA and the graphical representation of the anodic VOA comprises using different graphical features to distinguish the graphical representation of the cathodic VOA and the graphical representation of the anodic VOA.

14. The non-transitory computer-readable medium of claim 13, wherein using different graphical features comprises using a third graphical feature for any region in which the cathodic VOA overlaps the anodic VOA.

15. The non-transitory computer-readable medium of claim 10, wherein the modification controls comprise move, stretch, or compress controls to move, stretch, or compress the cathodic VOA or the anodic VOA relative to the lead.

16. The non-transitory computer-readable medium of claim 10, the actions further comprising displaying, on the display, a control for presenting an animation of the cathodic VOA or the anodic VOA for a time-varying stimulation.

17. The non-transitory computer-readable medium of claim 10, wherein
obtaining the cathodic VOA comprises obtaining cathodic VOAs for monopolar cathodic stimulation using a plurality of different sets of stimulation parameters;
obtaining the anodic VOA comprises obtaining anodic VOAs for monopolar anodic stimulation using the plurality of different sets of stimulation parameters; and
displaying the graphical representation of the cathodic VOA and the graphical representation of the anodic VOA comprises displaying, on the display, the graphical representations of the cathodic VOAs as a set of contour lines and the graphical representations of the anodic VOAs as a set of contour lines.

18. The non-transitory computer-readable medium of claim 10, wherein
obtaining the cathodic VOA comprises obtaining cathodic VOAs for monopolar cathodic stimulation using a plurality of different sets of stimulation parameters;
obtaining the anodic VOA comprises obtaining anodic VOAs for monopolar anodic stimulation using the plurality of different sets of stimulation parameters; and
displaying the graphical representation of the cathodic VOA and the graphical representation of the anodic VOA comprises displaying, on the display, the graphical representations of the cathodic VOAs using a first variation in shading or color and the graphical representations of the anodic VOAs using a second variation in shading or color.

19. A method for programming electrical stimulation of a patient using an implantable electrical stimulation system including an implantable pulse generator and a lead having a plurality of electrodes, the method comprising:
- determining which of a plurality of anatomical elements are activated by a threshold amount by monopolar cathodic stimulation using a set of stimulation parameters;
- determining which of the plurality of anatomical elements are activated by a threshold amount by monopolar anodic stimulation using the set of stimulation parameters;
- displaying, on a display, a graphical representation of the plurality of electrodes and a graphical representation of the plurality of anatomical elements, indicating which of the plurality of anatomical elements are activated by a threshold amount by the monopolar cathodic stimulation, which of the plurality of anatomical elements are activated by a threshold amount by the monopolar anodic stimulation, and which of the plurality of anatomical elements are not activated;
- when the set of stimulation parameters is modified using modification controls, determining which of the plurality of anatomical elements are activated by a threshold amount by the monopolar cathodic stimulation or the monopolar anodic stimulation using the modified set of stimulation parameters and modifying the graphical representations of the plurality of anatomical elements;
- programming the implantable pulse generator with the set of stimulation parameters or the modified set of stimulation parameters; and
- electrically stimulating the patient according to the set of stimulation parameters or the modified set of stimulation parameters using the implantable pulse generator and the plurality of electrodes of the lead.

20. The system of claim 19, wherein displaying the graphical representation of the plurality of anatomical elements comprises using different graphical features to distinguish the graphical representation of the plurality of anatomical elements activated by the monopolar cathodic stimulation and the graphical representation of the plurality of anatomical elements activated by the monopolar anodic stimulation.

* * * * *